US009223935B2

(12) United States Patent
Heneghan et al.

(10) Patent No.: US 9,223,935 B2
(45) Date of Patent: Dec. 29, 2015

(54) CONTACTLESS AND MINIMAL-CONTACT MONITORING OF QUALITY OF LIFE PARAMETERS FOR ASSESSMENT AND INTERVENTION

(75) Inventors: Conor Heneghan, Campbell, CA (US); Conor Hanley, Dun Iaoghaire (IE); Niall Fox, Tallamore (IE); Alberto Zaffaroni, Saronno (IT); Philip De Chazal, Dublin (IE)

(73) Assignee: ResMed Sensor Technologies Limited (IE)

( * ) Notice: Subject to any disclaimer, the term of this patent is extended or adjusted under 35 U.S.C. 154(b) by 0 days.

(21) Appl. No.: 13/120,640

(22) PCT Filed: Sep. 23, 2009

(86) PCT No.: PCT/US2009/058020
§ 371 (c)(1),
(2), (4) Date: Mar. 23, 2011

(87) PCT Pub. No.: WO2010/036700
PCT Pub. Date: Apr. 1, 2010

(65) Prior Publication Data
US 2011/0178377 A1     Jul. 21, 2011

Related U.S. Application Data

(60) Provisional application No. 61/099,792, filed on Sep. 24, 2008.

(51) Int. Cl.
*A61B 5/00*     (2006.01)
*G06F 19/00*     (2011.01)

(52) U.S. Cl.
CPC .......... *G06F 19/3418* (2013.01); *A61B 5/0002* (2013.01); *A61B 5/4806* (2013.01);
(Continued)

(58) Field of Classification Search
CPC ...... A61B 5/0002; A61B 5/72; A61B 5/7274; A61B 5/4806; G06F 19/345; G06F 19/3418
See application file for complete search history.

(56) References Cited

U.S. PATENT DOCUMENTS 2,634,413 A     4/1953   Potter
3,796,208 A     3/1974   Bloice
(Continued)

FOREIGN PATENT DOCUMENTS

CN     1737857 A     2/2006
CN     1739451 A     3/2006
(Continued)

OTHER PUBLICATIONS

PCT/US2009/058020 filed Sep. 23, 2009, Intl. Search Rpt & Written Opinion dated Dec. 2, 2009 (11 pages).
(Continued)

*Primary Examiner* — Bill Thomson
*Assistant Examiner* — Marie Archer
(74) *Attorney, Agent, or Firm* — Lerner, David, Littenberg, Krumholz & Mentlik, LLP (57) ABSTRACT

An apparatus, system, and method for the measurement, aggregation and analysis of data collected using non-contact or minimally-contacting sensors provides quality of life parameters for individual subjects, particularly in the context of a controlled trial of interventions on human subjects (e.g., a clinical trial of a drug, or an evaluation of a consumer item such as a fragrance). In particular, non-contact or minimal-contact measurement of quality-of-life parameters such as sleep, stress, relaxation, drowsiness, temperature and emotional state of humans may be evaluated, together with automated sampling, storage, and transmission to a remote data analysis center. One component of the system is that the objective data is measured with as little disruption as possible to the normal behavior of the subject. The system can also support behavioral and pharmaceutical interventions aimed at improving quality of life.

36 Claims, 8 Drawing Sheets

(52) U.S. Cl.
CPC .............. *A61B5/4815* (2013.01); *A61B 5/72*
(2013.01); *A61B 5/7271* (2013.01); *A61B 5/74*
(2013.01); *G06F 19/345* (2013.01); *G06F*
*19/36* (2013.01)

(56) References Cited

U.S. PATENT DOCUMENTS

| | | | |
|---|---|---|---|
| 3,911,899 A | 10/1975 | Hattes | |
| 3,993,995 A | 11/1976 | Kaplan et al. | |
| 4,085,740 A | 4/1978 | Allen, Jr. | |
| 4,513,748 A | 4/1985 | Nowogrodzki et al. | |
| 4,958,638 A * | 9/1990 | Sharpe et al. | 600/407 |
| 5,314,037 A | 5/1994 | Shaw et al. | |
| 5,361,070 A | 11/1994 | McEwan | |
| 5,549,113 A | 8/1996 | Halleck et al. | |
| 5,573,012 A | 11/1996 | McEwan | |
| 5,590,650 A | 1/1997 | Genova | |
| 5,671,733 A | 9/1997 | Raviv et al. | |
| 5,766,208 A | 6/1998 | McEwan | |
| 5,902,250 A | 5/1999 | Verrier et al. | |
| 5,966,090 A | 10/1999 | McEwan | |
| 5,995,856 A * | 11/1999 | Mannheimer et al. | 600/322 |
| 6,011,477 A | 1/2000 | Teodorescu et al. | |
| 6,062,216 A | 5/2000 | Corn | |
| 6,132,371 A | 10/2000 | Dempsey et al. | |
| 6,146,332 A | 11/2000 | Pinsonneault et al. | |
| 6,359,597 B2 | 3/2002 | Haj-Yousef | |
| 6,492,933 B1 | 12/2002 | McEwan | |
| 6,834,251 B1 | 12/2004 | Fletcher | |
| 6,839,581 B1 | 1/2005 | El-Solh et al. | |
| 6,932,769 B2 | 8/2005 | Griffin et al. | |
| 7,009,561 B2 * | 3/2006 | Menache et al. | 342/463 |
| 7,196,629 B2 | 3/2007 | Ruoss et al. | |
| 7,199,749 B2 | 4/2007 | Greneker, III et al. | |
| 7,272,431 B2 | 9/2007 | McGrath | |
| 7,387,607 B2 | 6/2008 | Holt et al. | |
| 7,428,468 B2 | 9/2008 | Takemura et al. | |
| 7,468,034 B2 | 12/2008 | Ouchi | |
| 7,473,228 B2 | 1/2009 | Griffin et al. | |
| 7,524,279 B2 | 4/2009 | Auphan | |
| 7,542,878 B2 | 6/2009 | Nanikashvili | |
| 7,679,545 B2 | 3/2010 | Rausch et al. | |
| 7,898,455 B2 | 3/2011 | Rosenbury | |
| 7,956,755 B2 | 6/2011 | Lee et al. | |
| 8,026,840 B2 | 9/2011 | Dwelly et al. | |
| 8,120,462 B2 * | 2/2012 | Shafer | 340/10.1 |
| 8,398,538 B2 | 3/2013 | Dothie et al. | |
| 8,428,696 B2 | 4/2013 | Foo | |
| 8,454,528 B2 | 6/2013 | Yuen et al. | |
| 2003/0092975 A1 | 5/2003 | Casscells et al. | |
| 2003/0201894 A1 | 10/2003 | Li | |
| 2004/0034289 A1 * | 2/2004 | Teller et al. | 600/300 |
| 2004/0073098 A1 | 4/2004 | Geva et al. | |
| 2004/0122489 A1 | 6/2004 | Mazar et al. | |
| 2004/0249258 A1 | 12/2004 | Tupin et al. | |
| 2004/0249296 A1 | 12/2004 | Ellscheid et al. | |
| 2005/0042589 A1 * | 2/2005 | Hatlestad et al. | 434/262 |
| 2005/0043645 A1 | 2/2005 | Ono et al. | |
| 2005/0073424 A1 | 4/2005 | Ruoss et al. | |
| 2005/0076908 A1 * | 4/2005 | Lee et al. | 128/204.23 |
| 2005/0119532 A1 | 6/2005 | Cloutier | |
| 2005/0119711 A1 | 6/2005 | Cho et al. | |
| 2005/0128124 A1 | 6/2005 | Greneker et al. | |
| 2005/0143617 A1 * | 6/2005 | Auphan | 600/26 |
| 2005/0240087 A1 | 10/2005 | Keenan et al. | |
| 2006/0079164 A1 | 4/2006 | DeCastro et al. | |
| 2006/0111635 A1 | 5/2006 | Todros et al. | |
| 2006/0189924 A1 | 8/2006 | Blakley et al. | |
| 2006/0241510 A1 | 10/2006 | Halperin et al. | |
| 2006/0270941 A1 | 11/2006 | Xie et al. | |
| 2007/0027367 A1 | 2/2007 | Oliver et al. | |
| 2007/0213620 A1 * | 9/2007 | Reisfeld | 600/484 |
| 2007/0296571 A1 * | 12/2007 | Kolen | 340/539.11 |
| 2008/0001735 A1 * | 1/2008 | Tran | 340/539.22 |
| 2008/0157956 A1 | 7/2008 | Radivojevic et al. | |
| 2008/0234568 A1 | 9/2008 | Ouchi | |
| 2008/0238757 A1 | 10/2008 | Lin et al. | |
| 2008/0269589 A1 | 10/2008 | Thijs et al. | |
| 2009/0256739 A1 | 10/2009 | Teshirogi et al. | |
| 2010/0099954 A1 * | 4/2010 | Dickinson et al. | 600/300 |
| 2011/0015495 A1 | 1/2011 | Dothie et al. | |
| 2011/0112425 A1 | 5/2011 | Muhlsteff et al. | |
| 2012/0245479 A1 | 9/2012 | Ganesh et al. | |
| 2013/0006124 A1 | 1/2013 | Eyal et al. | |
| 2013/0053653 A1 | 2/2013 | Cuddihy et al. | |
| 2013/0135137 A1 | 5/2013 | Mulder et al. | |
| 2013/0172770 A1 | 7/2013 | Muehlsteff | |

FOREIGN PATENT DOCUMENTS

| | | |
|---|---|---|
| CN | 1897871 A | 1/2007 |
| JP | 2000083927 A | 3/2000 |
| JP | 2004252770 A | 9/2004 |
| JP | 2005270570 A | 10/2005 |
| JP | 2007-098138 | 4/2007 |
| JP | 2008-071263 | 3/2008 |
| JP | 2008-506423 | 3/2008 |
| WO | 20040114193 A2 | 12/2004 |
| WO | 2005055824 A1 | 6/2005 |
| WO | 2006/054306 A | 5/2006 |
| WO | 2006090371 A2 | 8/2006 |
| WO | 2007052108 A2 | 5/2007 |
| WO | 2007117719 A2 | 10/2007 |
| WO | 2007/143535 A | 12/2007 |
| WO | 2008/057883 A | 5/2008 |
| WO | WO 2008096307 A1 * | 8/2008 |
| WO | 2009124297 A1 | 10/2009 |
| WO | 2010048310 A1 | 4/2010 |
| WO | 2010132850 A1 | 11/2010 |
| WO | 2012073183 A1 | 6/2012 |
| WO | 2013093712 A1 | 6/2013 |

OTHER PUBLICATIONS

"The Fundamentals of FFT-Based Signal Analysis and Measurement in LabVIEW and LabWindows/CVI" National Instruments, Published Jun. 8, 2009. 12 pages. Accessed Jan. 26, 2012. URL: http://zone.ni.com/devzone/cda/tut/p/id/4278#toc0.

Australian Examination Report for Application No. 2007256872 dated Mar. 20, 2012.

Boric-Lubecke et al., "Range correlation and I/Q performance benefits in single-chip silicon doppler radars for noncontact cardiopulmonary monitoring", IEEE Transactions on Microwave Theory and Techniques, vol. 52, No. 3, Mar. 2004.

Boric-Lubecke et al., "Range correlation effect on ISM band I/Q CMOS radar for non-contact vital signs sensing", IEEE MTT-S Digest, 2003.

Droitcour et al., "Range Correlation and I/Q Performance Benefits in Single-Chip Silicon Doppler Radars for Noncontact Cardiopulmonary Monitoring", IEEE Transactions on Microwave Theory and Techniques, Mar. 3, 2004, vol. 52, No. 3, pp. 838-848.

European Search Report and Search Opinion for European Patent Application No. 07784266.4, mailed Oct. 7, 2010.

Intenational Search Report for PCT International Application No. PCT/US2007/070196, mailed Feb. 22, 2008.

International Preliminay Report on Patentability for PCT International Application No. PCT/US2007/070196, mailed Dec. 3, 2008.

International Search Report and Written Opinion of the International Searching Authority for PCT International Application No. PCT/US2007/083155, Mailed Mar. 20, 2008.

Japanese Office Action dated Oct. 18, 2011 of Japanese Applicatikon No. 2009-513469 filed Jan. 30, 2009 (4 pages).

Japanese Office Action for Application No. 2009-513469 dated May 1, 2012.

Japanese Office Action for Application No. 2009-513469 dated Nov. 27, 2012.

Second Office Action dated Apr. 14, 2011 of Chinese Application No. 200780026740.0 filed Jan. 14, 2009 (16 pages).

US Office Action for U.S. Appl. No. 12/302,704 dated Sep. 16, 2012.

(56) References Cited

OTHER PUBLICATIONS

International Preliminary Report on Patentability for PCT International Patent Application No. PCT/US2009/058020, mailed on Aug. 31, 2010.
Japanese Decision of Rejection for Application No. 2011-528091 dated Dec. 3, 2013.
P. de Chazal, E. O'Hare, N. Fox, C. Heneghan, "Assessment of Sleep/Wake Patterns Using a Non-Contact Biomotion Sensor", Proc. 30th IEEE EMBS Conference, Aug. 2008, published by the IEEE, referred to on p. 9 of the specification.
Chinese Office Action for Application No. 2009801466909 dated Mar. 28, 2013.
Japanese Office Action for Application No. 2011-528091 dated Jul. 16, 2013.
Australian Examination Report for Application No. 2009296732 dated Oct. 9, 2014.
Chinese Office Action (Third) for Application No. 200980146690.9 dated Sep. 3, 2014.
Chinese Office Action for Application No. 200980146690.9 dated Feb. 17, 2014.
Japanese Office Action for Application No. 2011-528091 dated Mar. 3, 2015.

* cited by examiner

CONTACTLESS AND MINIMAL-CONTACT MONITORING OF QUALITY OF LIFE PARAMETERS FOR ASSESSMENT AND INTERVENTION

CROSS-REFERENCE TO RELATED APPLICATIONS

This is a U.S. National stage Application of PCT/US2009/058020 filed Sep. 23, 2009, which claims benefit of U.S. provisional application 61/099,792 filed Sep. 24, 2008, both of which are incorporated herein by their entireties.

BACKGROUND

This disclosure relates to the measurement, aggregation and analysis of data collected using non-contact or minimal-contact sensors together with a means for capturing subjective responses to provide quality of life parameters for individual subjects, particularly in the context of a controlled trial of interventions on human subjects (e.g., a clinical trial of a drug, or an evaluation of a consumer item such as a fragrance).

Monitoring of quality-of-life (QOL) parameters can be of importance when developing interventions aimed at improving a person's QOL. Quality-of-life parameters are measurements of general well-being which are generally accepted as being meaningful to an individual's perception of their life. In general QOL markers have a combination of an underlying objectively measurable elements, and a subjectively related element. Specific non-limiting examples include:

Sleep quality—an individual can subjectively report whether they are sleeping well or badly, and this has an impact on their perceived QOL. For a sleep quality QOL parameter, an objective measurement could be sleep duration, and a subjective input could be "how restful" the sleep was.

Stress—an individual can report on whether they find their current life circumstances to be stressful. For a stress QOL parameter, an objective measurement could be heart rate or cortisol levels; a subjective element could be a stress level questionnaire Relaxation—an individual can report the subjective sensation of being relaxed, which can also be objectively related to autonomic nervous system activity.

Pain—an individual can subjectively record levels of pain using a Pain Index [such as the Visual Analog Scale]. More objective measurements of pain can be obtained using a dolorimeter Body temperature—subjects can often report feelings of overheating or coolness which are not directly related to objective measurement of body core temperature.

Vigilance/drowsiness—vigilance, or attentiveness can also be measured objectively (e.g., using the psychomotor vigilance test) or through subjective questionnaires.

For clarification, a non-contact (or contactless) sensor is one which senses a parameter of a subject's physiology or behavior without any direct physical contact with a subject. Non-limiting examples include a movement detector based on radio-wave reflections, a microphone placed remotely from a subject, an infrared camera recording the surface temperature, or a faucet-monitor which records turning on of a faucet to wash hands. A minimal contact sensor may be considered to be one in which there is some physical contact with a sensor, but this is limited to short durations. Examples include a weight scale, a blood pressure monitor, a breath analyzer, or a hand-held surface ECG monitor. These minimal contact sensors can be distinguished from contact sensors typically used in clinical trials such as ECG patches, oximeters, EEG electrodes, etc, where there typically is adhesion to the body, and typically the sensor is intended for use over prolonged periods of time (e.g. >1 hour).

A key unifying factor in defining QOL parameters is the need to combine objective data from sensors, and subjective data from the monitored subject to assess the overall QOL. A particular challenge then arises when one wishes to measure the impact of an intervention on changes in QOL. For example, a company who has developed a drug to counteract sleep disruption will be interested to see if its drug has had any direct impact on a person's sleep which has resulted in either objectively or subjectively improved QOL. Similarly if a company has developed a product such as a skin emollient to reduce itchiness due to dry skin, they may wish to see if there has been an improved QOL (i.e., reduced scratching, lower level of discomfort) etc.

One commonly accepted means for answering such questions is to conduct a clinical or consumer trial which poses a statistical hypothesis which can be verified or rejected with a certain level of confidence. For example, in drug trials a double-blinded random controlled trial is a well accepted methodology for ascertaining the effect of drugs. However, measurement of QOL is difficult to conduct for a number of reasons, which various aspects of this disclosure can overcome: (a) it can be difficult to define a suitable measure for a QOL outcome, (b) by wearing a measurement device to measure QOL, one may directly impact on the exact quality-of-life parameter you wish to study, (c) there are logistical and financial challenges of measuring parameters in a natural "home" setting rather than in a formal laboratory setting. There are a variety of conventional techniques to measure some aspects of QOL which will now be discussed, together with their limitations.

Monitoring of a quality-of-life parameter can be motivated by a desire to integrate it into an intervention program. As an example, a person may undertake cognitive behavioral therapy (CBT) to reduce their stress-related quality of life. An important component of a CBT program is the ongoing assessment of the stress quality of life index, whose measurement will itself form part of the behavioral intervention. As a second example of an embodiment of the disclosure, we will describe a system for improving sleep quality through use of objective and subjective measurements of sleep quality-of-life indices.

As specific examples of the limitations of the current state of the art, consider the problem of measuring sleep quality in response to an anti-insomnia drug. Firstly, defining "sleep quality" as it relates to quality of life can be difficult, as this will often be a combination of objective and subjective measurements. Secondly, the current method favored for measuring sleep is to use a so-called polysomnogram which measures multiple physiological parameters (EEG, ECG, EOG, respiratory effort, oxygen level etc.). While the resulting physiological measurements are very rich, their measurement fundamentally alters the sleeping state of the subject (e.g., it is harder for them to turn over in bed), and cannot represent a true QOL sleep measurement. Finally, the current cost of the polysomnogram test (approximately $1500 in 2008) makes it an impractical tool for measurement of sleep quality in large numbers of subjects over long periods of time. Accordingly, there is a need for a system which can provide robust measurements of sleep quality-of-life in a highly non-invasive fashion. In an embodiment of our system, we describe one method for objectively measuring sleep quality using a totally non-invasive biomotion sensor. This can be combined with a number of subjective tools for measuring sleep quality, such as the Pittsburgh Sleep Quality Index and the Insomnia Severity Index (these consist of questionnaires on sleep habits such as time-to-bed, estimated time-to-fall-asleep etc.

Another QOL parameter of interest is stress level or, conversely, relaxation. Current techniques for objective measurement of stress include measurement of heart rate variability or cortisol levels. However, measurement of heart rate variability typically requires the subject to wear electrodes on the chest, which is often impractical for situations of daily living. Likewise, collection of cortisol samples to assess stress requires frequent collection of saliva samples, and is difficult to integrate into a daily living routine. There are also a number of widely used subjective measurements of stress or anxiety (e.g., Spielberger's State-Trait Anxiety Inventory). Accordingly, a method, system or apparatus which can reliably gather information about stress-related QOL parameters would have utility in a variety of settings.

Finally, measurement of the quality-of-life implications of chronic pain (such as chronic lower back pain) would have utility for assessing the benefit of therapies, or for providing cognitive feedback on pain management. Current subjective measurement tools such as the Oswestry Disability Index and the 36-Item Short-Form Health Survey are used to assess subjective quality of life in subjects with chronic pain conditions. Objective measurements of pain are not well defined, but there is some evidence that heart rate is correlated with pain intensity.

Accordingly, there is a clearly established need for systems and methods which measure quality-of-life outcomes in ambulatory/home settings, and which have minimal impact on the daily routine of the person whose QOL is being monitored. This is a particular need in clinical trials for non-contact or minimal contact sensors where the effects of interventions such as drugs, ointments, physiotherapy, nutriceuticals, behavior changes etc. are being evaluated.

SUMMARY

This disclosure provides various embodiments of an apparatus, system, and method for monitoring of quality-of-life parameters of a subject, using contact-free or minimal-contact sensors, in a convenient and low-cost fashion. The typical user of the system is a remote observer who wishes to monitor the QOL of the monitored subject in as non-invasive fashion as possible. The system typically includes: (a) one or more contactless or minimal-contact sensor units suitable for being placed close to where the subject is present (e.g., on a bedside table), (b) an input device for electronically capturing subjective responses such as a cell-phone, PDA etc., (c) a device for aggregating data together and transmitting to a remote location, (d) a display unit for showing information to the local user, and (e) a data archiving and analysis system for display and analysis of the quality-of-life parameters. The component (e) can also be used as a feedback device for interventional programs. For convenience, the sensor unit, input unit, data aggregation/transmission unit, and the display/monitoring unit can be incorporated into a single stand-alone unit, if desired (for example, all of these functions could be integrated on a cell-phone platform). The sensor units may include one or more of a non-contact measurement sensor (for detection of parameters such as sound, general bodily movement, respiration, heart rate, position, temperature), and one or more minimal contact sensors (e.g. weighing scales, thermometer). In one or more aspects of this disclosure, a system may incorporate a processing capability (which can be either at the local or remote sites) to generate quality-of-life parameters based on the objective and subjective measurements from a user. As a specific example, an overall sleep quality-of-life could be generated by combining the subjective response of the user to the Insomnia Severity Index together with an objective measurement of sleep duration.

In one or more embodiments, the disclosed approaches (pharmaceutical, device-based or behavioral) are useful in improving the quality-of-life parameters for these subjects. In particular, non-contact or minimal-contact measurement of quality-of-life parameters such as sleep, stress, relaxation, drowsiness, temperature and emotional state of humans is disclosed, together with means for automated sampling, storage, and transmission to a remote data analysis center. In one or more embodiments, one aspect of the system measures objective data with as little disruption as possible to the normal behavior of the subject.

In one particular embodiment, a quality-of-life monitoring system for human subjects, includes a plurality of multi-parameter physiological and environmental sensors configured to detect a plurality of physiological and environmental parameters related to a quality of life assessment, wherein each of said plurality of sensors either have no contact or minimal contact with a monitored subject; a timer that controls sampling of the detected parameters and allows a chronological reconstruction of recorded signals relating thereto; an input device which captures subjective responses from the monitored subject; a data storage device configured to record sampled signals; a data transmission capability so that data collected from a subject can be transmitted to a remote data monitoring center, and messages can be transmitted to the monitoring sensors; and a data monitoring and analysis capability so that overall quality-of-life parameters can be calculated based on the measured signals.

In another embodiment, a method for assessing a quality of life index includes measuring multi-parameter physiological and environmental parameters which are related to a quality of life assessment of a monitored subject with no contact or minimal contact with the monitored subject; collecting subjective responses from the monitored subject about their quality-of-life; analyzing objective and subjective measurements to generate a quantitative quality-of-life index; and generating suggested interventions to affect the measured quality of life index of the monitored subject.

BRIEF DESCRIPTION OF THE DRAWINGS

Embodiments of the disclosure will now be described with reference to the accompanying drawings in which.

DETAILED DESCRIPTION

Figure 1:
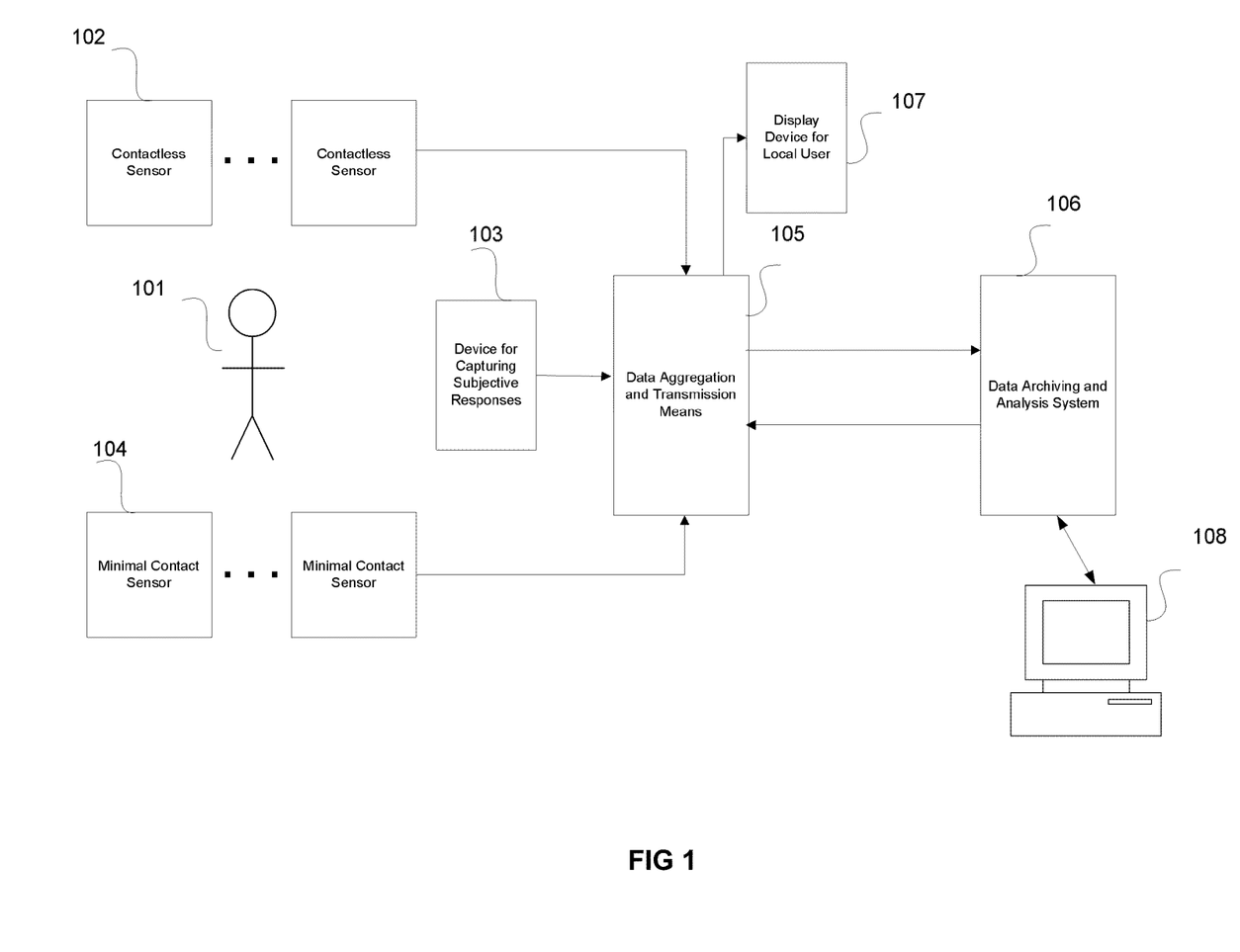
FIG. 1 is a diagram illustrating an overall schematic of an embodiment.

FIG. 1 is a diagram illustrating an overall schematic of an embodiment of this disclosure. Monitored subject 101 may be observed by a plurality of contactless 102 and minimal contact sensors 103. Subject 101 may also has access to input device 104 capable of obtaining subjective feedback from the subject through written text or recorded sound. Data aggregation and transmission device 105 collects the data from the sensors 102, 103 and 104, and may also control data sampling and input parameters used by the various sensors and devices. Optionally, display/feedback device 107 can be provided to the local user (e.g., this might indicate whether a signal is being collected from them, or give feedback on the most recent set of QOL parameters measured). Data aggregation and transmission device 105 may be configured to communicate in a bilateral way with remote data archiving and analysis system 106. Data archiving and analysis system 106 may store data from a plurality of subjects, and can carry out analysis of the recorded signals and feedback. It may also communicate with data display device 107 which can show the results of the analysis to a user, or with an optional separate display device 108 which shows the QOL parameters to a remote user.

Figure 2:
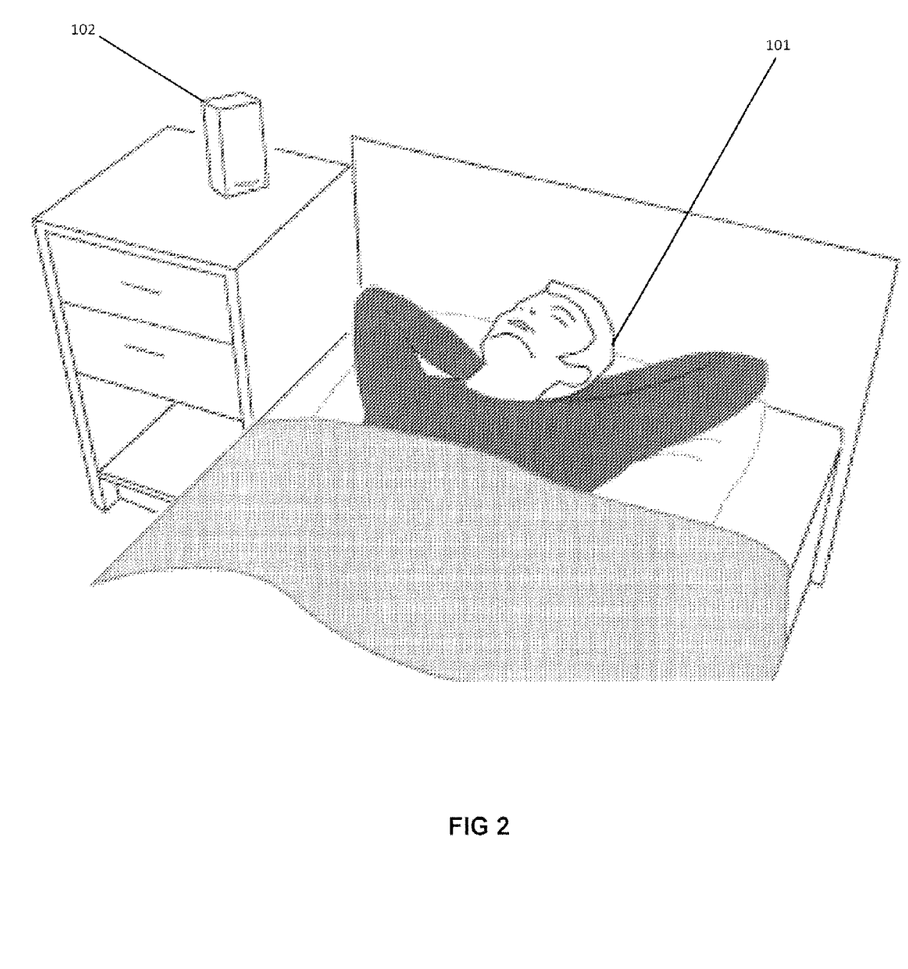
FIG. 2 is a specific example of an embodiment in which a contactless sensor is used to monitor the sleeping state of a subject, by placement in a nearby location (bedside locker)

FIG. 2 illustrates an embodiment of a contactless sensor that objectively monitors the sleeping state of a subject. In this embodiment, the sensor unit may contain one or more of a radio-frequency based biomotion sensor, a microphone (to pick up ambient sound), a temperature sensor (to pick up ambient temperature), a light sensor (to pick up ambient light levels), and an infrared detector for measuring the subject temperature. The contactless sensor may be placed on a bedside table, for example.

Figure 3:
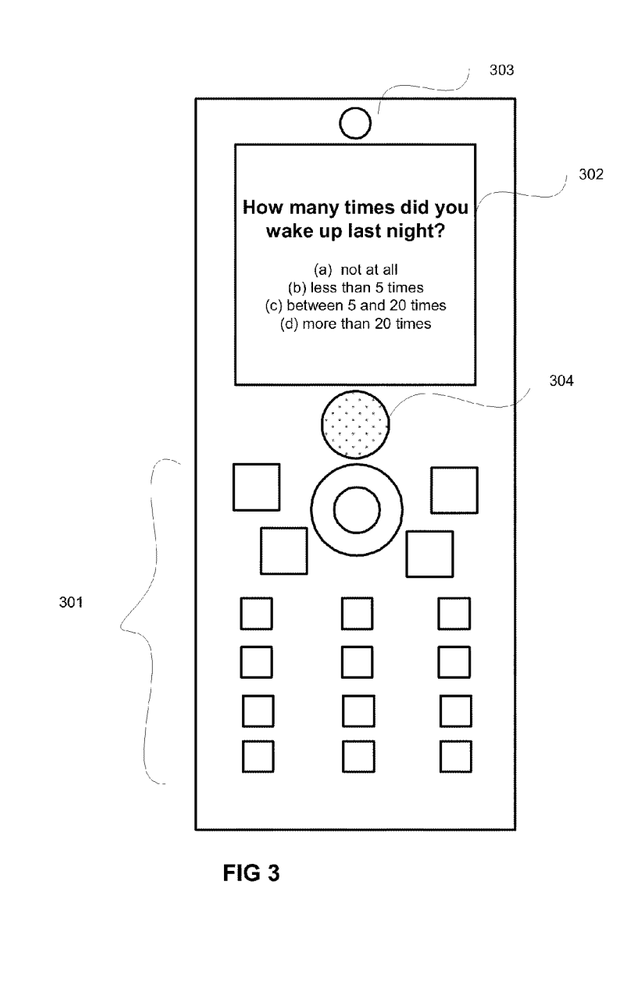
FIG. 3 is an example of an input device embodiment that could be used to capture subjective responses from individuals.

FIG. 3 illustrates an example of an embodiment of an input device for collecting user input. The input device would typically include alphanumeric keypad 301, display 302, microphone 303, and loudspeaker 304. This allows the generation of questions using either visual or audio means, and a person can then answer the questions using either text or audio input.

Figure 4:
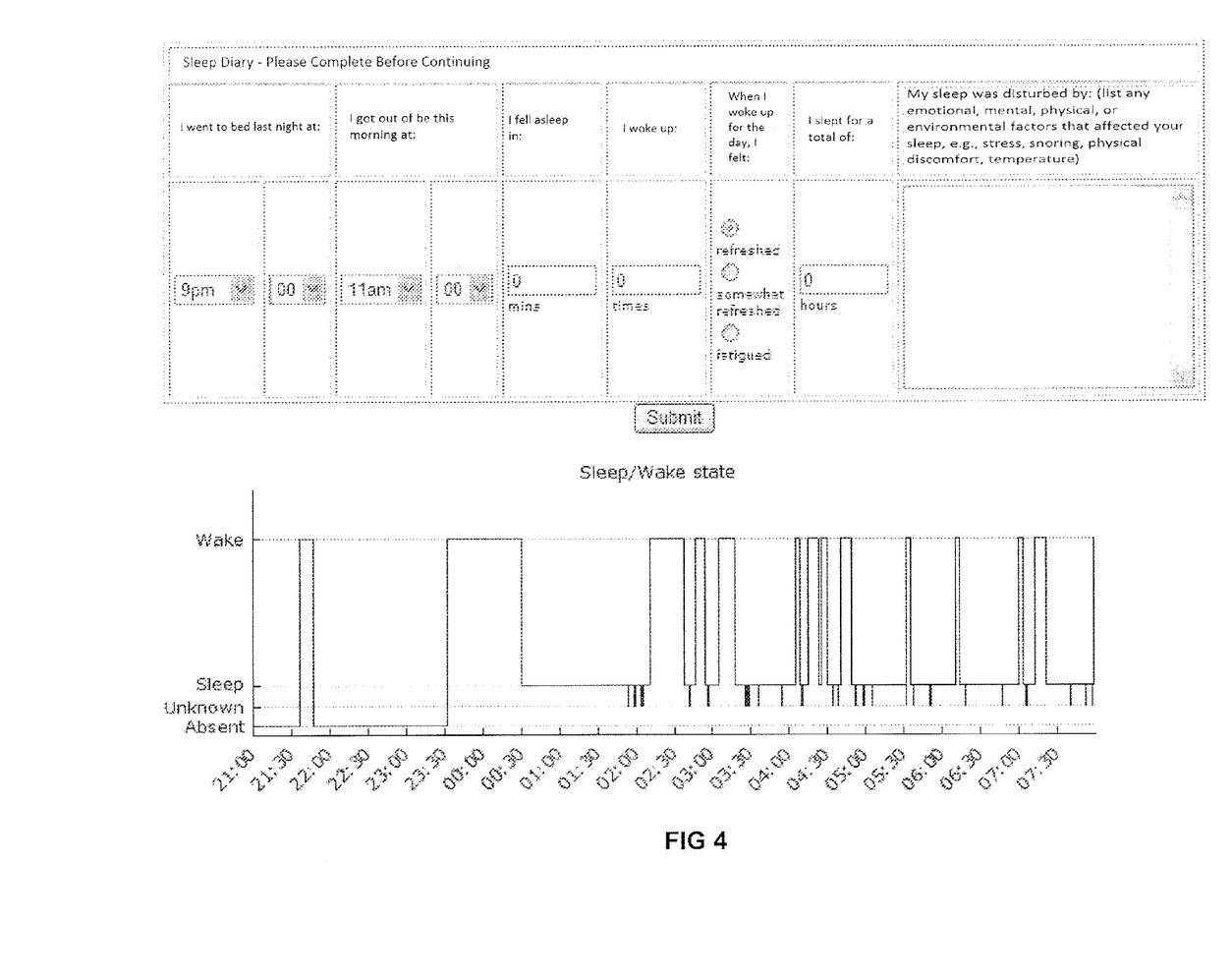
FIG. 4 is an alternative example of an embodiment in which a web-site could be used to capture the subjective responses from an individual.

FIG. 4 illustrates an embodiment using a personal computer with an internet browser to capture subjective perceptions of sleep.

Figure 5A:
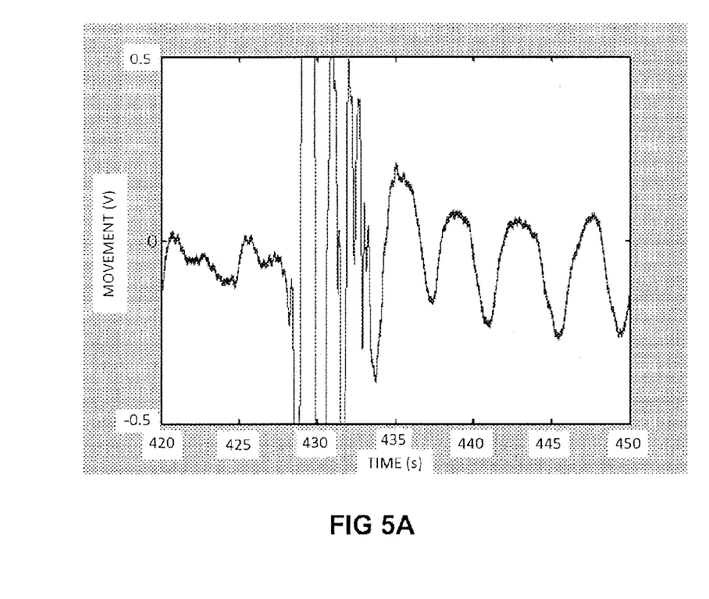
FIG. 5 is an example of an embodiment in which some of the raw data captured by a specific contactless sensor used in a sleep trial.
Figure 5B:
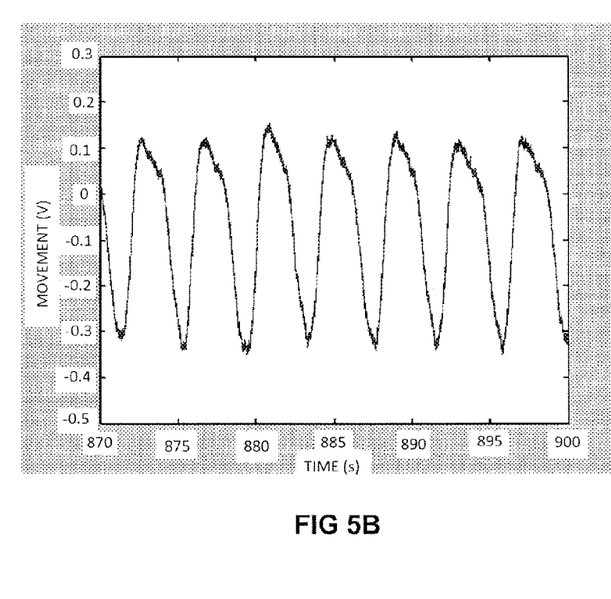

FIG. 5 provides an example of raw signals captured using a contactless sensor in a trial for measuring sleep quality-of-life. FIG. 4A shows the signal when a person is asleep and then turns over on their side. FIG. 4B shows the signal when the person is in deep sleep.

Figure 6:
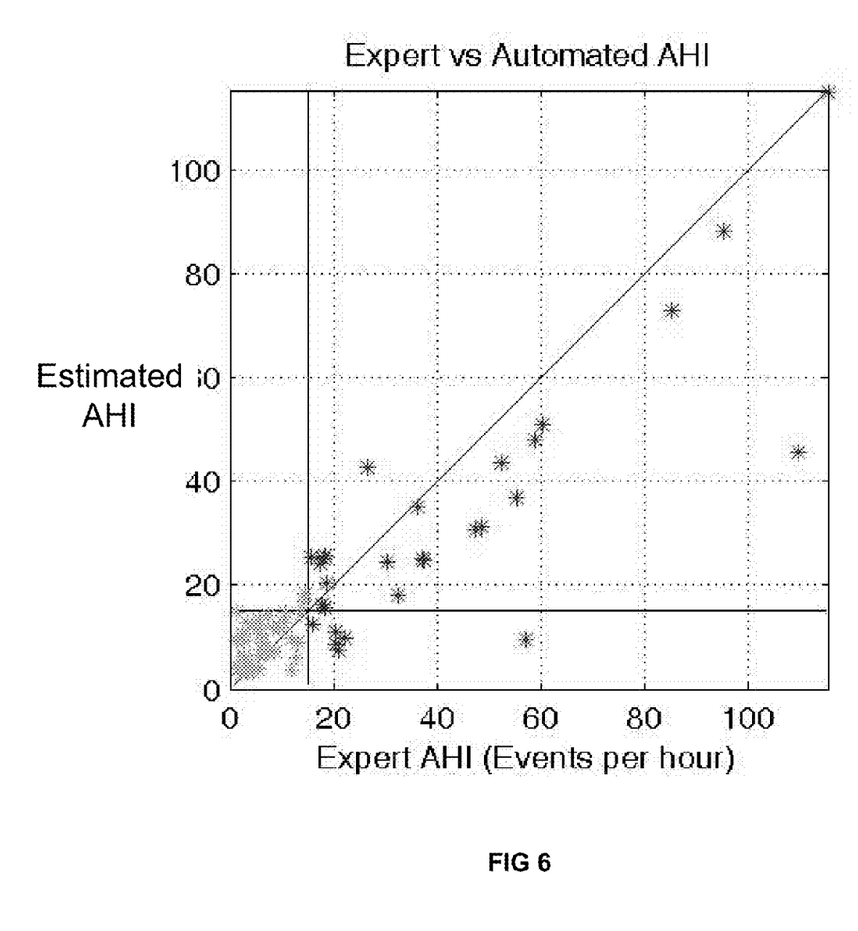
FIG. 6 shows example results of the system in measuring sleep apnea in a clinical trial.

FIG. 6 is an example of how the contactless system can estimate apnea-hypopnea index in a clinical trial with an accuracy similar to that of the current polysomnogram (PSG) estimates.

Figure 7A:
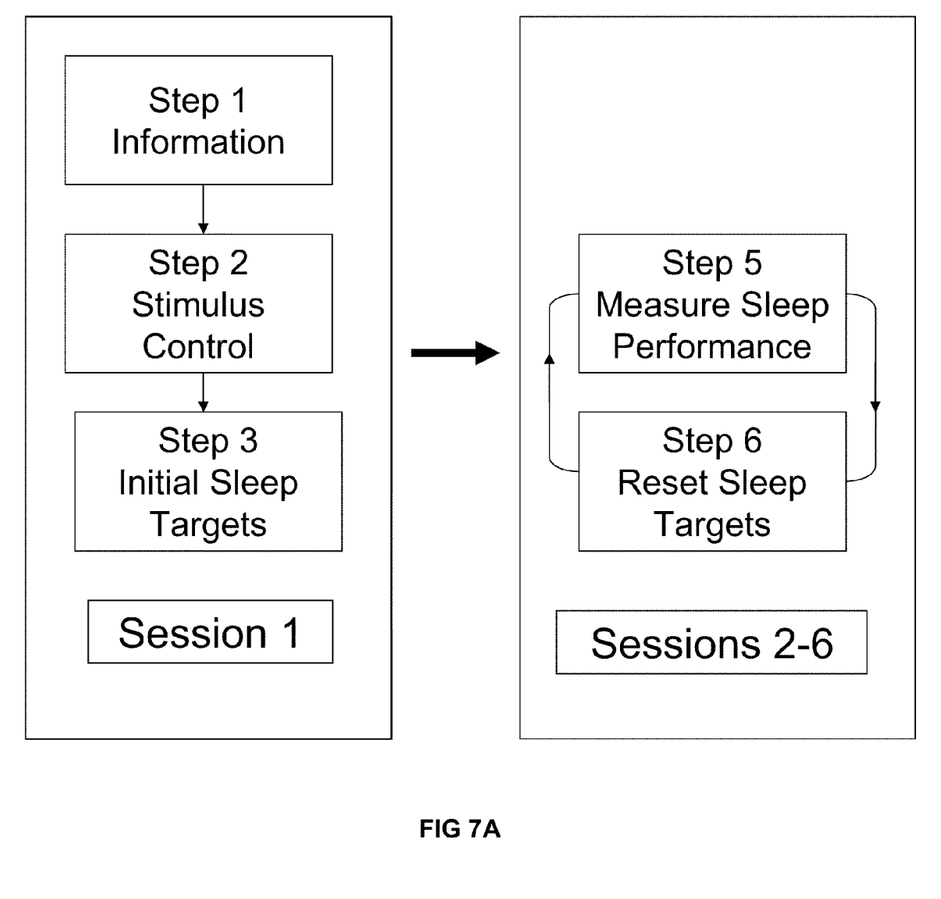
FIGS. 7A and 7B shows schematic representations of behavioral interventions based on one or more embodiments of this disclosure.

FIG. 7 is an example of a behavioral intervention based on use of the system to enhance sleep quality. FIG. 7(A) shows the components of a intervention based over several weeks, in which there is an initial session at which detailed information about sleep is provided, and the person is given the system for measurement of their sleep quality-of-life index (SQOLI).

Figure 7B:
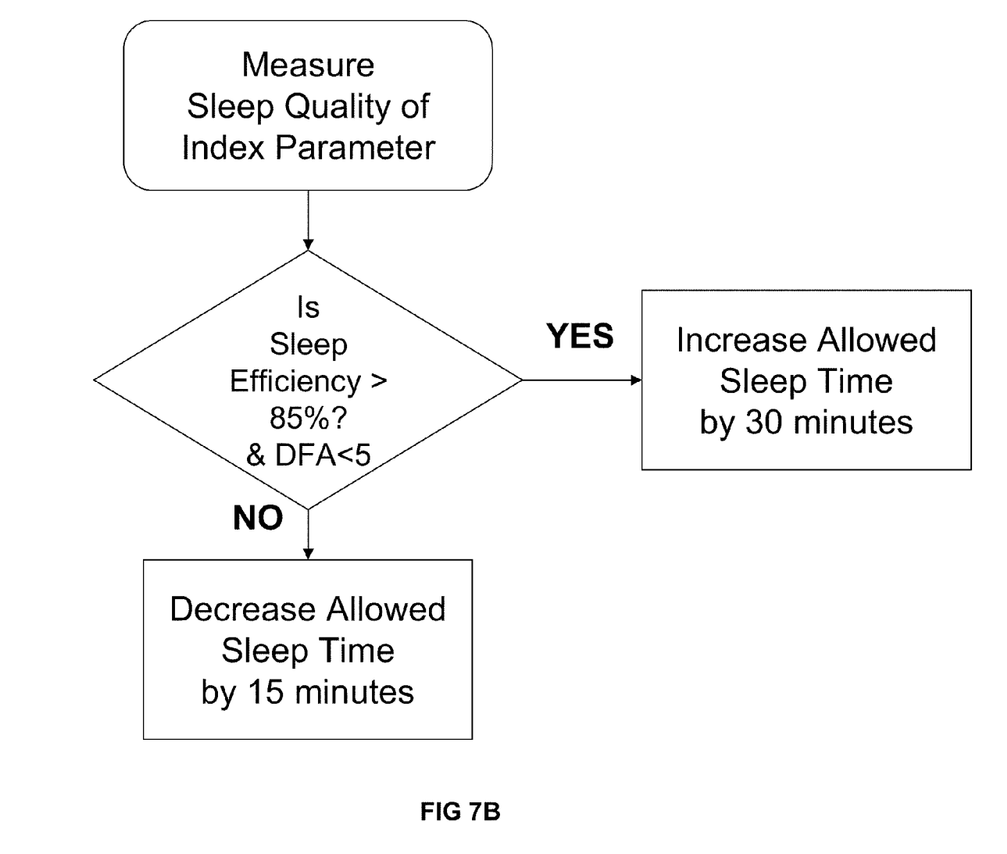

FIG. 7(B) shows an example of a specific algorithm that could be used within the intervention, based on the feedback from the SQOLI monitoring. For example, if they achieve an SQOLI greater than target, they can increase their time in bed by 30 minutes. If they fail, they can reduce time in bed by 15 minutes.

A typical embodiment of a system of this disclosure may include one or more non-contact sensors or minimal-contact sensors that can include one or more of the following:

(a) A biomotion sensor which measures movement, and which derives respiration, heart rate and movement parameters. An example of such a sensor is more fully described in the article written by P. de Chazal, E. O'Hare, N. Fox, C. Heneghan, "Assessment of Sleep/Wake Patterns Using a Non-Contact Biomotion Sensor", Proc. 30th IEEE EMBS Conference, August 2008, published by the IEEE, the entire contents of which are incorporated herein by reference. In one embodiment, the biomotion sensor may use a series of radio-frequency pulses at 5.8 GHz to generate echoes from a sleeping subject. The echoes may be mixed with the transmitted signals to generate a movement trace which includes movements due to breathing, heart rate, and positional changes.

(b) An audio sensor which measures ambient sound. A specific example of a microphone appropriate for inclusion in the system would be the HK-Sound Omni, −27 dB microphone with part number S-OM9765C273S-C08.

(c) A temperature sensor which measures environmental temperature (typically to ±1 C). A specific example of a temperature sensor appropriate for inclusion would be the National Semiconductor LM20, SC70 package.

(d) A light level sensor would measure light level. A specific example of a light level sensor appropriate for inclusion is the Square D® Clipsal Light-Level Sensor.

(e) A body-temperature measuring sensor. A specific example of a sensor that may be used in the system is the body thermometer Part No. 310 from the YuanYa Far Asia Company.

The minimal contact sensors may include one or more of the following:

(a) A weighing scales for measuring body weight. A specific example is the A&D UC-321PBT.

(b) A blood pressure device, such as the A&F UA767PBT.

(c) A continuous positive airway pressure device for treating sleep apnea, such as the ResMed Autoset Spirit S8.

(d) A pedometer for measuring step-counts (such as the Omron Pocket Pedometer with PC software, HJ-7201TC).

(e) A body-worn accelerometer for measuring physical activity during the day (such as the ActivePAL device).

(f) A body composition analyzer such as the Omron Body Composition Monitor with Scale, HBF-500, which calculates visceral fat and base metabolic rate.

(g) Other contactless or minimally contacting devices could also be included.

In one or more embodiments, the system may include a data-acquisition and processing capability which provides a logging capability for the non-contact and minimal-contact sensors described above. This typically could include, for example, an analog-to-digital converter (ADC), a timer, and a processor. The processor may be configured to control the sampling of the signals, and may also apply any necessary data processing or reduction techniques (e.g., compression) to minimize unnecessary storage or transmission of data.

A data communication subsystem may provide communication capability which could send the recorded data to a remote database for further storage and analysis, and a data analysis system including, for example, a database, can be configured to provide processing functionality as well as input to a visual display.

In one specific embodiment of the system, data acquisition, processing, and communications can utilize using, for example, a Bluetooth-enabled data acquisition device (e.g. the commercially available BlueSentry® device from Roving Networks). Other conventional wireless approaches may also be used. This provides the ability to sample arbitrary voltage waveforms, and can also accept data in digital format.

In this embodiment, the Bluetooth device can then transmit data to a cell phone using the Bluetooth protocol, so that the data can be stored on a cell-phone memory. The cell phone can also carry out initial processing of the data. The cell phone can also be used as a device for capturing subjective data from the user, using either a text-based entry system, or through a voice enabled question-and-answer system. Subjective data can also be captured using a web-page.

The cell phone can provide the data transmission capability to a remote site using protocols such as GPRS or EDGE. The data analysis system is a personal computer running a database (e.g., the My SQL database software), which is capable of being queries by analysis software which can calculate useful QOL parameters. Finally a data display capability can be provided by a program querying the database, the outputs of the analytical program and using graphical or text output on a web browser.

As an example of the clinical use of a specific embodiment, the system was used to measure quality-of-life related to sleep in a specific clinical trial scenario. A group of 15 patients with chronic lower back pain (CLBP), and an age and gender matched cohort of 15 subjects with no back pain were recruited. After initial screening and enrollment, study participants completed a baseline assessment. Gender, age, weight, height, BMI and medication usage were recorded. All subjects completed baseline self report measures of sleep quality (Pittsburgh Sleep Quality Index Insomnia Severity Index [16], quality of life (SF36v2) [17] and pain as part of the SF36v2 questionnaire (bodily pain scale of the SF36v2). The CLBP subjects also completed the Oswestry Disability Index (ODI) as a measure of functional disability related to their low back pain. All subjects then underwent two consecutive nights of objective monitoring using the non-contact biomotion sensor mentioned above, while simultaneously completing a subjective daily sleep log; the Pittsburgh Sleep Diary. Table 1 shows some objective measurements of sleep using the system, and includes the total sleep time, sleep efficiency, sleep onset latency. Other objective parameters which could be measured would include: number of awakenings (>1 minute in duration) and wake-after-sleep-onset.

TABLE 1

Objective sleep indices obtained using the system

| Variable | Control Group (mean ± sd) | CLBP Group (mean ± sd) | p-value |
|---|---|---|---|
| Total sleep time (mins) | 399 (41) | 382 (74) | 0.428 |
| Sleep Efficiency (%) | 85.8 (4.4) | 77.8 (7.8) | 0.002 |
| Sleep Latency (mins) | 9.4 (10.2) | 9.3 (11.1) | 0.972 |

The objective sleep indices described in Table 1 were obtained using a sleep stage classification system that processed the non-contact biomotion sensor data to produce sleep and awake classifications every 30 seconds. This was developed using the following observations:

Large movements (e.g., several cm in size) can be easily recognized in the non-contact signal. Bodily movement provides significant information about the sleep state of a subject, and has been widely used in actigraphy to determine sleep/wake state. The variability of respiration changes significantly with sleep stage. In deep sleep, it has long been noted that respiration is steadier in both frequency and amplitude than during wakefulness of REM sleep.

Accordingly, a first stage in processing of the non-contact biomotion signal was to identify movement and respiration information. To illustrate how this is possible, FIG. 4A shows an example of the signal recorded by the non-contact sensor when there is a significant movement of the torso and arms due to the person shifting sleeping position. An algorithm based on detection of high amplitude and frequency sections of the signal was used to isolate the periods of movement.

For periods where there is no significant limb or torso movement, respiratory-related movement is the predominant recorded signal and estimates of breathing rate and relative amplitude are obtained using a peak and trough identifying algorithm. FIG. 4B illustrates the signal recorded by the sensor during a period of Stage 4 sleep that demonstrates a steady breathing effort.

To validate the performance of the system in correctly labeling 30-second epochs, we recorded signals simultaneously with a full polysomnogram (PSG) montage. We compared the sleep epoch annotations from the PSG and the non-contact biomotion sensor and report the overall classification accuracy, sleep sensitivity and predictivity, wake specificity and predictivity. The overall accuracy is the percentage of total epochs correctly classified. The results are shown in Table 2, and provide evidence that the system can objectively measure sleep with a high degree of accuracy.

TABLE 2

Accuracy of objective recognition of sleep state using the contactless method

| Overall | | By sleep state | |
|---|---|---|---|
| Awake | 69% | Awake | 69% |
| Sleep | 87% | REM | 82% |
| Pred. of Awake | 53% | Stage 1 | 61% |
| Pred. of Sleep | 91% | Stage 2 | 87% |
| Accuracy | 82% | Stage 3 | 97% |
| | | Stage 4 | 98% |

Table 3 shows some of the subjective measurements from the same subjects, and includes their subjective assessment of sleep duration, sleep efficiency, number of awakenings, and sleep latency for each night, as well as their overall PSQI and ISI scores.

TABLE 3

Subjective sleep indices obtained using the system

| Variable | Control Group (mean ± sd) | CLBP Group (mean ± sd) | p-value |
|---|---|---|---|
| Pittsburgh Sleep Quality Index | 2.1 (2.1) | 11.7 (4.3) | <0.001 |
| Insomnia Severity Index | 2.8 (4.6) | 13.4 (7.3) | <0.001 |
| Estimated Sleep Onset Latency | 11.7 (4.3) | 45.3 (27.7) | <0.001 |
| Estimated Sleep Efficiency | 95.3 (5.8) | 73.4 (16.5) | <0.001 |
| Estimated Night Time Awakenings ≥3 | 2/15 | 15/15 | <0.001 |

The system can report these subjective and objective measurements of sleep but, in one aspect, it can also report parameters related to overall Sleep Quality of Life Index (SQOLI) which combines objective and subjective measurements. There are a number of ways in which this could be done. For example, we could define the following SQOL indices:

$SQOL$ duration = {0.8 × OBJECTIVE SLEEP DURATION +

0.2 × OBJECTIVE SLEEP DURATION}

$SQOL$ fragmentation =

{(number of periods of objectively measured wakefulness >

1 minute + reported self awakenings/objective sleep duration}

$$SQOL \text{ latency} = \sqrt{\frac{\text{OBJECTIVE SLEEP LATENCY} \times}{\text{SUBJECTIVE SLEEP LATENCY}}}$$

The skilled user will be able to construct other combined measurements of sleep quality of life which capture the most meaningful outcomes for a particular application.

In another embodiment, the system may be used to capture quality-of-life in patients with chronic cough (e.g., patients suffering from chronic obstructive pulmonary disease). In this embodiment, two contactless sensors may be used: the non-contact biomotion sensor described above, and a microphone. The system can measure objectively sounds associated with each coughing episode, and the respiratory effort associated with each cough. This provides a more accurate means of collecting cough frequency than relying on sound alone. There are also subjective measurements of cough impact on quality of life (e.g., the parent cough-specific QOL (PC-QOL) questionnaire described in "Development of a parent-proxy quality-of-life chronic cough-specific questionnaire: clinical impact vs psychometric evaluations," Newcombe P A, Sheffield J K, Juniper E F, Marchant J M, Halsted R A, Masters I B, Chang A B, Chest. 2008 February; 133(2): 386-95).

As another exemplary embodiment, the system could be used as a screening tool to identify sleep apnea severity and incidence in a clinical trial setting. In this embodiment, the contactless biomotion sensor is used to detect periods of no-breathing (apnea) and reduced amplitude breathing (hypopnea). FIG. 5 shows the estimated sleep apnea severity of the patients enrolled in a clinical trial, prior to therapy, as an example of how the system can be used.

The user skilled in the art will realize that the system can be used in a number of clinical trial settings where measurement of quality-of-life is important. As specific examples of such uses, we can consider:

Measurement of sleep quality of life in patients with atopic dermatitis (AD). Subjects with AD often have poor quality of life due to daytime itchiness combined with poor sleep quality due to subconscious scratching during sleep. In a clinical trial designed to assess the impact of an intervention such as a new drug or skin-cream, the system can be used to capture subjective and objective quality of life parameters as a final outcome measure. The outcome of the sleep quality-of-life index measurement can be a recommendation on whether to use a certain active medication, and the dosage of that medication.

Measurement of sleep quality in infants in response to feeding products. For example, lactose intolerance is known to affect quality-of-life in babies due to disrupted sleep, stomach pain, and crying episodes. Feeding products which aim to overcome lactose intolerance can be assessed by combination of objective sleep indices plus parent-reported crying episodes, to form an overall quality-of-life index.

As a further specific embodiment, sleep quality can be enhanced by providing a behavioral feedback program related to sleep quality of life. A person self-reporting insomnia can use the system as follows to enhance their sleep quality of life.

On a first visit with a physician, a person can self-report general dissatisfaction with their sleep quality of life. They can then choose to undertake a cognitive behavioral therapy program in the following steps.

Step 1: They undertake an induction session with a therapist or self-guided manual. In this induction step, the individual is introduced to information about basic physiological mechanisms of sleep such as normal physiological sleep patterns, sleep requirements, etc. This step ensures there are no incorrect perceptions of sleep (i.e. a person believing that 3 hours sleep a night is typical, or that you must sleep exactly 8 hrs per day for normal health).

Step 2: Bootzin stimulus control instructions. In this step, subject-specific information is established, and basic behavioral interventions are agreed. For example, firstly, the subject and therapies agree a target standard wake-up time (e.g., 7 AM). They then agree behavioral interventions such as getting out of bed after 20 minutes of extended awakening, and the need to avoid sleep-incompatible bedroom behavior (e.g., television, computer games, . . . ). They may agree to eliminate daytime naps.

Step 3: Establish initial target. Based on discussions above, the patient and therapist may then agree a sleep quality of life index (SQOLI) which will act as a target. As a specific example, the SQOLI may be based on achieving 85% sleep efficiency and a subjective "difficulty falling asleep" rating of <5 (on a 1-10.scale where 10 is very difficult and 1 is easy) The behavioral program will then consist of a week in which the patient tries to achieve the target based on going to bed 5 hours before the agreed wake-up time (e.g. at 2 AM in our example). The disclosure we have described above in FIGS. 1 to 5 provides the objective measurements of sleep efficiency and combines with the subjective user feedback to produce an SQOLI. At the end of the first week, the patient and therapist review the SQOLI measurements and determine the next step.

Step 4: Feedback loop based on Sleep Quality of Index. If the subject has achieved the desired SQOLI in the first week, then a new target is set. As a specific example, the subject will now go to bed 5.5 hours before the agreed wake up time, but will still try to achieve the same targets of 85% sleep efficiency and "difficulty falling asleep" metric <5. In subsequent weeks, the algorithm will be applied that the person can increase their sleep time by 30 minutes, provided they have met the targets in the previous week. This process can continue until a final desired steady state sleep quality of life index is reached (e.g., sleeping 7.5 hrs per night with a sleep efficiency of >85%).

The person skilled in the art will realize that a number of behavioral interventions have been developed and described in the literature for improving sleep quality. However a limitation of all these current approaches is that they do not have a reliable and easy means for providing the sleep quality of life metric, and it is this limitation which the current disclosure overcomes. Furthermore, the person skilled in the art will also realize that a number of pharmaceutical interventions are appropriate for improvement of sleep quality (e.g. prescription of Ambien®), and that the disclosure described here can support these medical interventions also.

STATEMENT OF INDUSTRIAL APPLICABILITY

The apparatus, system and method of this disclosure finds utility in contactless and minimum contact assessment of quality-of-life indices in clinical and consumer trials, and in interventions to improve the quality of life.

What we claim is:

1. A system for monitoring the quality of life of humans, comprising:
    at least one physiological sensor configured to wirelessly receive a signal reflected from a subject indicative of measured data, derive measured data from the reflected signal, and to wirelessly transmit the measured data to a handheld portable device;

the handheld portable device comprising:
- an interface for collecting subjective data from the subject, wherein the subjective data comprises sleep quality data and other quality of life data; and
- a transmitter configured to transmit the measured data transmitted by the at least one physiological sensor and the subjective data collected from the interface to a remote data monitoring center for calculating one or more of a sleep quality of life duration, fragmentation, efficiency, and latency index value on the basis of the measured data and subjective data transmitted to the remote data monitoring center.

2. The system of claim 1, further comprising at least one environmental sensor configured to measure data indicative of environmental parameters.

3. The system of claim 2, wherein the at least physiological or environmental sensor is arranged at least 50 cm from the subject being monitored to provide an open space therebetween.

4. The system of claim 2, wherein the at least one physiological or environmental sensor is not directly mechanically coupled to the subject.

5. The system of claim 1 wherein the measured data pertains to sleep quality.

6. The system of claim 1 wherein the measured data comprises an objective measurement of sleep combined with a subjective assessment of sleep.

7. The system of claim 1 wherein the measured data is an objective measurement of sleep.

8. The system of claim 1, wherein the portable handheld device further comprises a receiver configured to receive, from the remote data monitoring center, a recommendation provided to the subject, the recommendation being based on the calculated quality of life index value.

9. The system of claim 8, wherein the remote data monitoring center is further configured to:
- receive the measured data and subjective data transmitted from the handheld portable device;
- calculate the quality of life index value and generate the recommendation to be provided to the subject, based on the calculated quality of life index value; and
- transmit the recommendation to the handheld portable device.

10. The system of claim 1, wherein the handheld device further comprises:
- a processor that performs initial processing of the measured data and the subjective data; and
- wherein the transmitter transmits the initially processed measured data and subjective data to the remote data monitoring center for archiving and analysis.

11. The system of claim 10, the system further comprising:
- a receiver to receive a recommendation from the remote data monitoring center based on the initially processed measured data and subjective data; and
- an output to provide the recommendation to the subject.

12. A method for monitoring the quality of life of humans, comprising:
- receiving, at a handheld portable device, objective data measured from at least one non-contact or minimal contact physiological or environmental sensor;
- collecting, via an interface of the portable handheld device, subjective quality of life data from a subject;
- transmitting, via the handheld portable device, the objective data and the subjective quality of life data to a remote data monitoring center to facilitate calculation of a quality of life index as a function of at least the measured objective data and the subjective quality of life data, the quality of life index including one or more of a sleep duration index value, a sleep latency index value, or a sleep fragmentation index value; and
- receiving, at the handheld portable device, from the data monitoring center a recommendation provided to the subject, the recommendation being based on a calculated quality of life index, wherein the calculated quality of life index includes one or more of a sleep duration index value, a sleep latency index value, or a sleep fragmentation index value.

13. The method of claim 12, wherein the objective data pertains to sleep.

14. The method of claim 12, wherein the subjective quality of life data pertains to sleep.

15. The method of claim 12, wherein measured objective data is collected by the at least one non-contact or minimal contact physiological or environmental sensor that is arranged more than 50 cm from the monitored subject.

16. The method of claim 12, wherein the objective data is collected with no direct mechanical coupling between the at least one non-contact or minimal contact physiological or environmental sensor and the subject.

17. The method of claim 12, wherein the recommendation pertains to a future behavior of the subject, wherein the method further comprises:
- receiving at least one additional objective data or collecting at least one additional subjective quality of life data; and
- comparing current values of the data to past values of the data.

18. The method of claim 12, wherein the recommendation pertains to a potential change in a pharmaceutical dosing.

19. The method of claim 12, wherein the subjective quality of life data further comprises sleep quality data.

20. The method of claim 12, wherein the method further comprises performing, at the handheld device, initial processing of the objective data and the subjective quality of life data; and the step of transmitting further includes transmitting the initially processed objective data and subjective quality of life data to the data monitoring center for archiving and further processing.

21. The method of claim 20, wherein the method further comprises providing, via the handheld device, the recommendation to the subject and wherein the received recommendation from the data monitoring center is based on further processed objective data and subjective quality of life data.

22. A method for assessing a quality of life index, the method comprising:
- obtaining, at a handheld portable device, at least one objective measurement of physiological or environmental data, wherein the objective measurement is obtained with non-contact or minimal contact with a monitored subject;
- receiving, at the handheld portable device, at least one subjective response from the monitored subject about their quality of life;
- calculating a quality of life index as a function of the objective measurement and the subjective response the quality of life index including one or more index values for sleep duration, fragmentation, and latency;
- querying a database using the quality of life index; and
- providing a recommendation to the monitored subject, by way of the handheld portable device, the recommendation being provided in response to querying the database with the quality of life index.

23. The method of claim 22, wherein the subjective response further comprises sleep quality data.

24. The method of claim 22, wherein the at least one objective measurement is a physiological or environmental parameter related to a quality of life assessment of the monitored subject.

25. The method of claim 24, wherein the physiological or environmental parameter is collected by sensing elements arranged more than 50 cm from the monitored subject.

26. The method of claim 24, wherein the physiological or environmental parameter is collected with no direct mechanical coupling between sensing elements and the monitored subject.

27. The method of claim 22, wherein the at least one objective measurement pertains to sleep.

28. The method of claim 22, wherein the subjective response pertains to sleep.

29. The method of claim 22, wherein the recommendation pertains to a future behavior of the monitored subject.

30. The method of claim 22, further comprising:
    obtaining at least one additional objective measurement; and
    comparing a current value to a past value thereof.

31. The method of claim 22, wherein the recommendation pertains to pharmaceutical dosing.

32. The method of claim 22, wherein at least one subjective response is received from the monitored subject on an interface of the handheld portable device.

33. The method of claim 22, further comprising the steps of:
    transmitting, by the handheld portable device, the objective measurement or subjective response to a remote data monitoring center for analysis.

34. The method of claim 33, further comprising the steps of:
    receiving, at the handheld portable device, the recommendation for the monitored subject; and
    displaying, at the handheld portable device, the recommendation to the monitored subject.

35. A method for assessing a quality of life index, the method comprising:
    receiving transmitted objective quality of life data obtained by way of at least one sensor and subjective quality of life data from a monitored subject;
    electronically generating, using a portable handheld device, a numerical metric which represents a quality of life index, as a function of the received objective and subjective quality of life data the metric including one or more of a sleep duration, fragmentation, or latency; and
    electronically generating a recommendation for the monitored subject in response to querying the database with the numerical metric.

36. The method of claim 35, further comprising the step of transmitting the recommendation to the monitored subject.

* * * * *